(12) United States Patent
Alfano et al.

(10) Patent No.: US 8,082,024 B2
(45) Date of Patent: Dec. 20, 2011

(54) MICRO-SCALE COMPACT DEVICE FOR IN VIVO MEDICAL DIAGNOSIS COMBINING OPTICAL IMAGING AND POINT FLUORESCENCE SPECTROSCOPY

(76) Inventors: Robert R. Alfano, Bronx, NY (US); Alvin Katz, Bronx, NY (US); Scott Alfano, Bronx, NY (US)

( * ) Notice: Subject to any disclaimer, the term of this patent is extended or adjusted under 35 U.S.C. 154(b) by 1744 days.

(21) Appl. No.: 11/037,961

(22) Filed: Jan. 18, 2005

(65) Prior Publication Data
US 2005/0215911 A1   Sep. 29, 2005

Related U.S. Application Data

(60) Provisional application No. 60/536,723, filed on Jan. 16, 2004.

(51) Int. Cl.
*A61B 6/00* (2006.01)
(52) U.S. Cl. .......................... 600/476; 600/473
(58) Field of Classification Search .................. 600/300, 600/407, 473–480; 128/903; 348/68, 76–77
See application file for complete search history.

(56) References Cited

U.S. PATENT DOCUMENTS

| | | | | |
|---|---|---|---|---|
| 4,170,987 A * | 10/1979 | Anselmo et al. | ............... | 600/475 |
| 4,930,516 A * | 6/1990 | Alfano et al. | ................. | 600/477 |
| 5,131,398 A * | 7/1992 | Alfano et al. | ................. | 600/476 |
| 5,348,018 A * | 9/1994 | Alfano et al. | ................. | 600/476 |
| 5,395,366 A * | 3/1995 | D'Andrea et al. | ......... | 604/890.1 |
| 5,604,531 A * | 2/1997 | Iddan et al. | ...................... | 348/76 |
| 5,701,902 A * | 12/1997 | Vari et al. | ....................... | 600/473 |
| 5,800,350 A * | 9/1998 | Coppleson et al. | ........... | 600/372 |
| 5,833,603 A * | 11/1998 | Kovacs et al. | ................. | 600/317 |
| 6,091,985 A * | 7/2000 | Alfano et al. | ................. | 600/476 |
| 6,240,312 B1 * | 5/2001 | Alfano et al. | ................. | 600/476 |
| 6,324,418 B1 * | 11/2001 | Crowley et al. | ................. | 600/476 |
| 6,950,690 B1 * | 9/2005 | Meron et al. | ................. | 600/424 |
| 6,984,205 B2 * | 1/2006 | Gazdzinski | .................... | 600/160 |
| 7,650,180 B2 * | 1/2010 | Glukhovsky et al. | ......... | 600/476 |
| 2002/0103417 A1 * | 8/2002 | Gazdzinski | .................... | 600/109 |
| 2002/0177779 A1 * | 11/2002 | Adler et al. | ................. | 600/476 |
| 2002/0198439 A1 * | 12/2002 | Mizuno | ......................... | 600/109 |
| 2003/0020810 A1 * | 1/2003 | Takizawa et al. | ................. | 348/68 |
| 2003/0023150 A1 * | 1/2003 | Yokoi et al. | .................... | 600/300 |
| 2004/0152988 A1 * | 8/2004 | Weirich | ......................... | 600/473 |
| 2006/0155193 A1 * | 7/2006 | Leonardi et al. | ............... | 600/473 |

* cited by examiner

*Primary Examiner* — Sanjay Cattungal
(74) *Attorney, Agent, or Firm* — The Farrell Law Firm, P.C.

(57) ABSTRACT

An apparatus and method for medical practitioners to detect the presence of abnormal cells including cancerous and precancerous cells by using a transport capsule containing an imaging apparatus including UV sources and fluorescence detectors for obtaining images and fluorescence data of biological cells and tissue. The method includes the steps of scanning biological tissue using an ultra-violet (UV) source to obtain fluorescence data, transferring fluorescence data and/or images using a radio frequency (RF) or other suitable means to a personal computer (PC) system, analyzing the image and/or fluorescence data in the PC, identifying -tissues with precancerous and cancerous cells, and optionally determining their precise location, and assessing the accuracy of the calculated fluoroscopic images.

21 Claims, 9 Drawing Sheets

MICRO-SCALE COMPACT DEVICE FOR IN VIVO MEDICAL DIAGNOSIS COMBINING OPTICAL IMAGING AND POINT FLUORESCENCE SPECTROSCOPY

PRIORITY

This application claims priority to a provisional patent application entitled "Micro-Scale Compact Device For In Vivo Medical Diagnosis Combining Optical Imaging And Point Fluorescence Spectroscopy", filed in the United States Patent and Trademark Office on Jan. 16, 2004 and assigned U.S. Ser. No. 60/536,723, the contents of which are hereby incorporated by reference.

BACKGROUND OF THE INVENTION

1. Field of the Invention

The present invention relates generally to a medical imaging apparatus for biological tissue visualization and assessment and more particularly to a medical imaging apparatus and method for the detection of abnormal biological tissue including cancerous and precancerous cellular regions of arteries for detection of arterial disease.

2. Description of the Related Art

With the pervasiveness of cancer in modem times, it has become common to screen the aeorodigestive tract, gynecological (GYN) tract and breast(s) for malignancies. There are many ways to screen these sites including X-Ray imaging, MRI (magnetic resonance imaging), CT (computer tomography) scanning, and endoscopy. Disadvantages of X-Ray imaging, MRI and CT scanning include time consumption, high cost and harmful radiation exposure. Moreover X-Ray imaging, MRI and CT scanning cannot provide detailed photographic images of surfaces of sampled tissue when desired.

Endoscopy is a well-known method to screen for malignancies and uses an endoscope with an embedded optical fiber (or fiber bundle). A light from a light source is coupled into the fiber or fiber bundle and delivered through the endoscope to illuminate tissue located at a distal end of the endoscope. The light scattered from the tissue is collected by a one or more lenses and either imaged into a detector mounted on the distal end of the endoscope or coupled into an imaging fiber bundle. The image is then transmitted through the endoscope to an imaging means such as a computer or video system for examination by a physician, and for storage, printing, transmission, etc. as desired. During the procedure, if abnormal tissues are visually detected, a medical practitioner can acquire tissue specimens for biopsies and treatment. Moreover, as tissue samples are usually only taken at sites which have visual evidence of a malignancy, the detection of pre-cancerous, or early stage cancerous tissue is delayed, which can have catastrophic results.

Currently, endoscopy is an invasive method of imaging which requires that the patient be anesthetized and which can cause discomfort or pain to the patient after the procedure. Moreover, endoscopy is expensive and time consuming, and cannot immediately confirm the presence of cancer cells or pre-cancerous cells. Furthermore, the removal of tissue specimens for biopsies can cause additional discomfort or pain to the patient after the procedure.

Recently, there have been several advances in the field of endoscopy which were aimed at solving some of endoscopy's disadvantages. For example, a technology using native tissue fluorescence for detection of cancer and precancer cells by exciting a tissue with UV and/or visible light from an optical source (e.g., lasers, LEDs, lamps, etc.) and detecting the emission by photo-detectors has been developed. Because carcenogenesis modifies the molecular and structural properties of cells and tissues, resulting in changes of the cells' and tissues' optical properties, abnormal cells (e.g., precancerous and cancerous cells) can be optically detected. For example, fluorescence signatures from key tissue fluorophores, such as aromatic amino acids, collagen, elastin, reduced nicotinnamide adenine dinucleotide (NADH) and flavins, can accurately and immediately distinguish normal tissues from malignant and pre-malignant tissues. This optical detection method does not require tissue acquisition and subsequent in-vitro biopsies, which greatly reduces patient discomfort and can allow for immediate detection of cancer. The immediate detection of cancer can be life-saving, as any reduction in time in the diagnosis of cancer can reduce the likelihood of the progression of the cancer—especially when dealing with highly malignant cancer. This technology was invented by the inventor of the present invention and is described in U.S. Pat. No. 4,930,516, entitled, "Method For Detecting Cancerous Tissue Using Visible Native Luminescence,"U.S. Pat. No. 5,131,398 entitled, "Method And Apparatus For Distinguishing Cancerous Tissue From Benign Tumor Tissue, Benign Tissue Or Normal Tissue Using Native Fluorescence," and U.S. Pat. No. 6,091,985 entitled, "Detection Of Cancer And Precancerous Conditions In Tissues And/Or Cells Using Native Fluorescence Excitation Spectroscopy," all to R. R. Alfano, et al., the contents of all of which are incorporated herein by reference.

Although the use of a point source fluorescence for the detection of cancer has been demonstrated in areas of the body which do not require the use of a endoscope, such as areas of the gynecological (GYN) tract, aerodigestive tract, colon, breast and esophagus, in vivo fluorescence imaging through an endoscope has presented formidable problems such as: currently available imaging endoscopes use imaging fibers manufactured from glass and therefore cannot transmit the required UV and blue light; detectors located on the distal end of endoscopes have poor UV spectral response; and fluorescence signals in UV and blue light are weaker than scattered light and thus require electronic amplification.

Another technology to improve the screening of the aeorodigestive tract employs a remotely controllable micro-scale imaging device as a replacement to endoscopy. This technology has the potential to greatly reduce the invasiveness of endoscopy and to allow access to harder-to-reach organs such as the small intestine. This technology was invented by the inventor of the present invention and is disclosed in U.S. Pat. No. 6,240,312 B1, entitled, "Compact Photonics Explorer," to R. R. Alfano, et al., the contents of which are incorporated herein by reference.

Unfortunately, the use of fluorescence spectroscopy and imaging in a single micro-scaled device capable of both visually imaging and assessing tissue needs improvement.

SUMMARY OF THE INVENTION

The present invention is directed to improving the aforesaid problems which occur in the prior art and to provide an apparatus and a method for the timely, non-invasive and accurate detection of tissue and cell normalities and abnormalities, including pre-cancer, cancer arteriosclerosis, and the like.

In order to accomplish the above object, according to an embodiment of the present invention, there is provided an apparatus and method for detecting tissue malignancies (such pre-cancer, cancer and the like) using fluorescence spectroscopy and an imaging system that can function throughout the aerodigestive tract using at least one point source for fluorescence.

In other embodiments of the present invention, the diagnostic potential of currently existing CCD (charge coupled device) endoscopes is improved by adding UV-visible light-emitting diodes (LEDs) and photodiodes with filters to the endoscope tip (i.e., the distal end) to provide real-time spectroscopic information and to make it possible to diagnose tissues in situ.

In yet other embodiments of the present invention, there is provided compact photonic explorer (CPE) including an optical imaging system, UV and visible-light-emitting diodes (LEDs) and/or UV emitting lasers, and photodiodes with filters in order to provide real-time images including spectroscopic information and make it possible to diagnose tissues in situ.

In other embodiments of the present invention, a compact photonics explorer (CPE) apparatus and method suitable for in vivo applications is provided, the device including a compact printed circuit board (PCB) having an imaging optical detector, one or more point source optical detectors, one or more light sources, a transmitter, and a microprocessor-based controller printed upon the PCB.

In yet other embodiments of the present invention, there is provided a system and method for conserving power usage and to extend battery life by acquiring images in a pulsed mode operation wherein the duty cycle of the light sources and the data and/or image transmission rates can be adjusted to extend the battery's lifetime and to provide a desired amount of data.

In further embodiments of the present invention, a combination of fluorescence targeting of abnormal tissue and visible imaging of abnormal tissue can provide for superior imaging and assessment for medical purposes.

In yet other embodiments of the present invention, the imaging apparatus of the present invention can be included with an endoscope as desired.

Therefore, according to a first aspect of the present invention, there is provided a micro-scaled apparatus for visually assessing and detecting abnormalities in biological tissue in vivo, the apparatus including: an illumination source for providing illumination in the visible spectrum, an optical image sensor for visible light imaging, an emitter for emitting an optical beam having an excitation wavelength suitable for causing biological tissue to emit native fluorescence at an emission wavelength, an optical detector for detecting the native fluorescence, a processing circuit for controlling the emitter and optical detector, a transmitter for transmitting data received from the optical detector and from the optical image sensor to a remote receiver, the transmitter being controlled by the processing circuit, and a transport capsule for containing at least the optical light source(s) and/or optical detector(s).

According to another aspect of the present invention, there is provided a method for visually assessing and detecting abnormalities in biological tissue in vivo, the method including the steps of: illuminating and obtaining a visual image of biological tissue using a visible light emitter, and emitting an optical beam having an excitation wavelength suitable for causing biological tissue to emit native fluorescence at an emission wavelength characteristic of the biological tissue using at least one emitter, detecting the native fluorescence from biological tissue using at least one detector, and transmitting data related to the detected native fluorescence to a remote receiver.

According to another aspect of the present invention, there is provided a method for detecting cancer and pre-cancer, the method including the steps of: illuminating the biological tissue with visible light and obtaining a visible light image of the biological tissue, exciting the biological tissue using at least two excitation wavelengths so that the biological tissue emits native fluorescence at a given emission wavelength corresponding to the at least two excitation wavelengths, detecting the intensity of the native fluorescence at an emission wavelength for at least two of the emission wavelengths, and comparing a ratio of the detected intensities to a predetermined threshold to determine the presence of at least one of cancer or precancer.

BRIEF DESCRIPTION OF THE DRAWINGS

The above and other objects, features and advantages of the present invention will become more apparent from the following detailed description when taken in conjunction with the accompanying drawings in which.

DETAILED DESCRIPTION OF THE PREFERRED EMBODIMENT

A preferred embodiment of the present invention will now be described in more detail.

The present invention is directed to the use of a medical imaging and assessment apparatus and method including CMOS or CCD sensors, UV light sources, UV/visible point sensors, visible light sources, at least one visible imaging detector, dispersion selection components, and beam steering components (e.g., lenses, gratings, mirrors, prisms, optical fibers, beam-splitters, combinations of these, or like) to image an area of tissue combined with point fluorescence spectroscopy of the area in order to image and detect and distinguish normal areas from abnormal areas (e.g., areas having pre-cancerous and cancerous cells and the like). Moreover, the present invention provides data (e.g., image and fluorescence information including fluorescence intensity) to the operator (e.g., a surgeon, or other medical provider) in real time for real-time diagnosis and detection of abnormalities such as pre-cancer and cancer in biological tissue. Moreover, the present invention does not require the acquisition of tissue samples and subsequent biopsies for tissue assessment, thus saving time, reducing cost, and possibly saving lives—especially when dealing with highly malignant cells with the potential for metastasis.

The fluorescence information acquired from tissue are detected, and a ratio of the fluorescence information (e.g., the fluorescence intensity ratio (FIR)) is computed and transmitted to a desired receiver (e.g., PDA, mobile terminal, a computer, PalmOne Tungsten T5™, mini-PC, etc.) using radio frequency (RF), or other suitable means (e.g., electrical wires, optical means, microwaves, etc.), for assessment. The assessment can be made at any location to which the data can be transmitted (e.g., at a computer terminal located at the side of the patient (e.g., worn by the patient) or in another part of the world. Moreover, the visual images can also be transmitted to a desired receiver (e.g., a computer, display, etc.) as desired. Furthermore, the ratio of the fluorescence information (or any other indicator containing image and/or fluorescence information) can be optionally associated with a visible image (either before or after transmission). In alternative embodiments, the ratio of the fluorescence information is calculated by a remote computer to which the data is transmitted.

The visible light source can include red, green and blue LEDs either emitting simultaneously to provide white-light illumination or emitting sequentially (for providing spectral images). Moreover, the visible light source can include a UV-emitting LED with phosphors to produce a white light. The visible imaging detector can include a CMOS or CCD detector array. The dispersion selection components can include absorbing filters, interference filters or holographic filters. The beam steering optics can include lenses, gratings, mirrors, prisms, optical fibers, beam-splitters, other diffractive components, combinations of these, or like.

The UV-visible light sources of the present invention can include lasers or LEDs based on alloys of AlGaN, AlGaInN or ZnMO (or other suitable materials) emitting to excite native tissue fluorophores. The UV/visible point sensors can include phototransistors or photodiodes (e.g., PIN, PN or avalanche) or other suitable devices (such as CMOS, CCD image sensors where light energy is integrated to obtain one or more signals from a region or tissue to capture the desired image.

Figure 1:
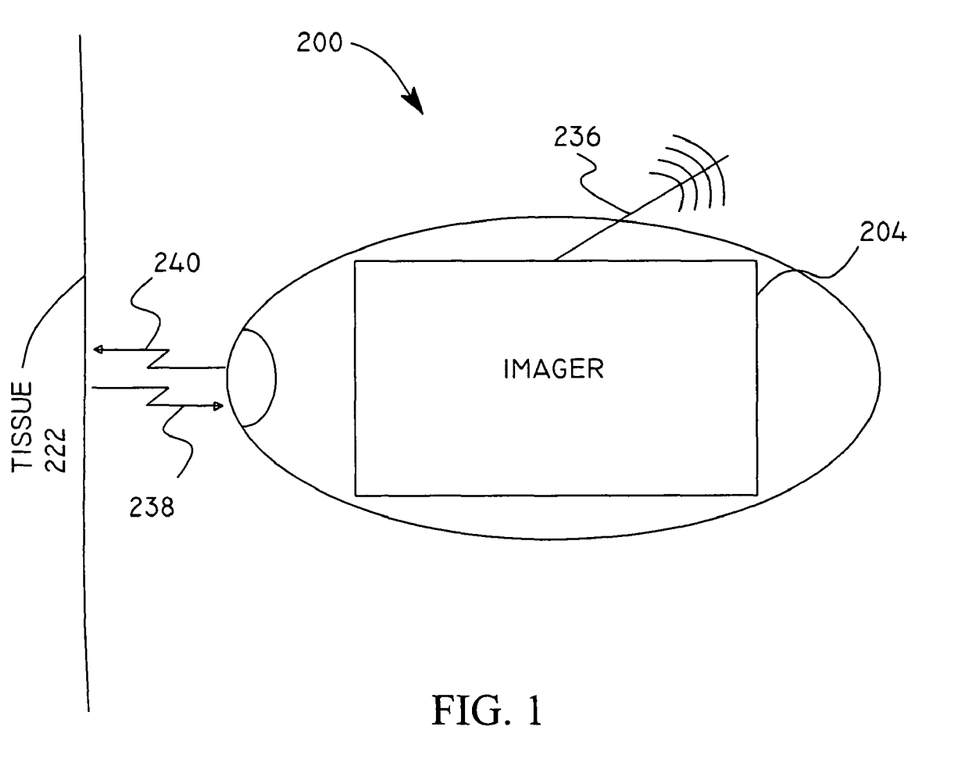
FIG. 1 is a perspective view illustration of a compact photonic explorer (CPE) according to an embodiment of the present invention.

A perspective view illustration of a compact photonic explorer (CPE) according to an embodiment of the present invention is shown in FIG. 1. The CPE 200 includes an imager 204 and a transmitter 236 as will be described below. Although the CPE 200 can be propelled by peristaltic motion, in alternative embodiments, an optional propulsion system (e.g., a propeller or other motive means such as tracks, etc.) can be used. It should be noted that although the imager 204 is shown encompassed by the CPE, optical elements and RF elements (as will be shown and described below) of the imager 204 can be in communication with the exterior of the CPE as may be required. The transmitted and incident light beams are indicated by lines 240 and 238, respectively.

In yet other alternative embodiments, MEMS (Micro-electromechanical systems)-based devices can be mounted to or within the CPE for providing control of the optical system (e.g., adjusting filtering, beam-steering, etc.), and for providing locomotion to the CPE.

Figure 2:
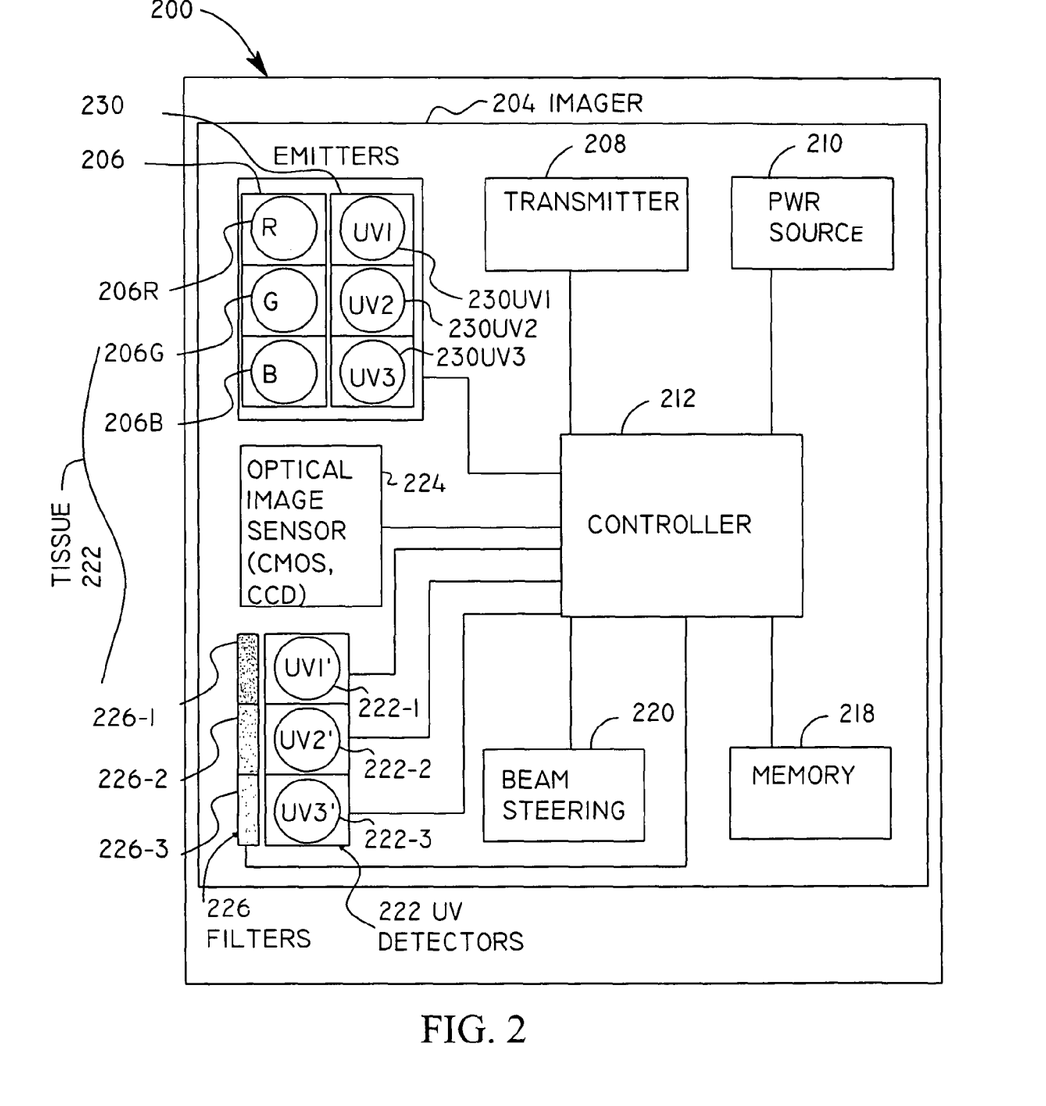
FIG. 2 is a block diagram of an embodiment of the present invention illustrating a compact photonic explorer (CPE) including visible imaging and UV-visible point detectors.

A block diagram of an embodiment of the present invention illustrating a CPE including visible imaging and UV-visible point detectors is shown in FIG. 2. The CPE 200 is located adjacent to a tissue sample 202 which will be imaged and assessed in vivo. The CPE 200 includes imager 204 which is used to obtain phosphorescent information and optional still and video images and to transmit this information to a desired device (e.g. a computer, imager, etc.). The imager 204 includes visible light emitters (also known as an illumination source) 206, UV-visible light emitters 230 an RF transmitter and optional receiver for control functions 208, a power source 210, controller 212, memory 218, UV detectors 222, filters 226, and an optical image sensor 224. Lenses (not shown) may be necessary for each light source, and can include multi-element lenses as well as other suitable lenses which can focus and pass desired wavelengths.

The visible light emitter 206 includes a plurality of emitters for providing visible light including a red emitter 206R, a green emitter 206G, a blue emitter 206B which can be manufactured using a red LED, a green LED, and a blue LED, respectively. A combination LED can emit white light for color imaging,. But, in alternative embodiments the visible light emitter can include a single source such as a white LED or other suitable light source. The UV light emitter 230 includes a plurality of UV emitters for providing UV illumination including a first UV emitter 230UV1, a second UV emitter 230UV2, and a third UV emitter 230UV3, which can be manufactured using any suitable technology. The optical image sensor 224 includes a optical image sensor (e.g., a CMOS, CCD, diode array, phototransistors, PIN diodes, photodiodes, etc.) and a UV/visible point detector or other suitable photo detector. The point photo detector is suitable for detecting visible and UV fluorescence light being emitted from the tissue 202. Wavelength selection components such as gratings (not shown) and filters 226 are used to filter the light as desired and will be described below. Beam steering components (e.g., lenses, gratings, etc.) 220 are used to precisely locate and/or focus desired optical beams.

A power source 210 is used to provide power to various components of the imager 204 and preferably includes storage sources such as a battery and/or capacitors, as well as other known sources. It should be noted that in order to conserve power, the duty cycles of the imager 204 including the visible light emitters 206, UV-visible light emitters 230 an RF transmitter 208, controller 212, memory 218, UV detectors 222, filters 226, and an optical image sensor 224, can be set to desired intervals.

The controller 212 controls the various functions of the imager 204 including optional timing circuits (not shown) which are used for timing and powering the emitters and for sampling the detectors (e.g., gating the detectors). For example, the controller 212 controls the timing of the visible and UV emitters 206 and 230, respectively, and the gating of the detectors 222-1, 222-2 and 222-3). Moreover, the controller 212 controls the RF transmitter 208 so that data can be transmitted from the imager 204 to other locations. The data can be sent in either analog form or in digital form if an analog-to-digital (A/D) converter (not shown) is used.

An optional memory 218 (e.g., a RAM, ROM, etc.) interfaces with the controller and is used for storing and retrieving necessary data (e.g., code to control the imager 204, image data, etc. as required).

In the current embodiment of the present invention, there preferably between one to three UV emitters 230UV1, 230UV2 and 230UV3, and three UV point detectors 222-1, 222-2 and 222-3, which can be tissue specific so as to optimize the diagnostic potential and power usage of the imager 204. But, in alternative embodiments, different emitters (e.g., emitters having different wavelengths) and corresponding detectors can be used depending upon the application (e.g., GYN tract, aerodigestive tract, GI tract, etc. as desired). The bandpass of the filters (or other dispersive elements ) can be selected to match the emission wavelengths of interest. In alternative embodiments any number of UV emitters can be used as desired.

The wavelengths of each UV emitter can be chosen to excite different tissue fluorophores to interrogate the structure and molecular composition of the tissue and to provide information about the health of the interrogated tissue. For example, wavelengths in the range of 260-300 nm are ideal for interrogating tissue for tryptophan; wavelengths in the range of 325-350 nm are ideal for interrogating tissue for collagen; and wavelengths in the range of 250-400 nm are ideal for interrogating tissue for NADH. The UV detectors 222 are optimized for detection of spectral information in the UV and blue light regions. Preferably the number of UV detectors 222 is chosen to match the number of fluorescent wavelengths having diagnostic information. Optical filters 226 and/or transmission or reflection gratings (not shown) are used as desired to restrict the wavelengths incident upon the UV detectors 222 to specific fluorophores. For example, the detector wavelength can be 320-360 nm for tryptophan; 370-400 nm for collagen and 430-470 nm for NADH. Likewise the number of detectors can be chosen to match the number of fluorescent wavelengths having diagnostic information.

Figure 3:
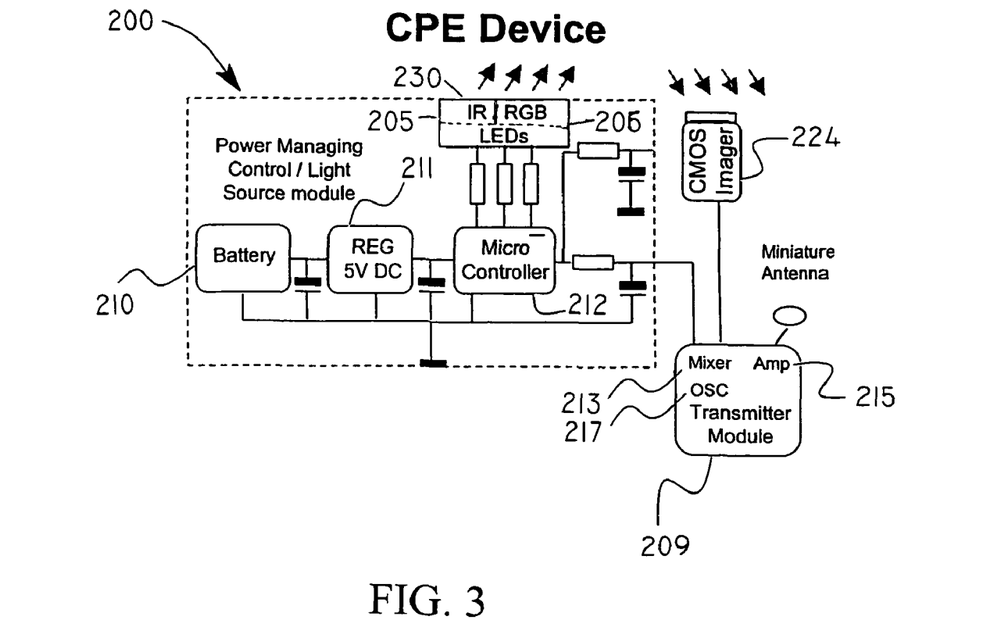
FIG. 3 is a block diagram of an alternative embodiment of the present invention illustrating a compact photonic explorer (CPE) including visible imaging and IV-visible point detectors.

A block diagram of an alternative embodiment of the present invention illustrating a CPE including visible imaging and UV-visible point detectors is shown in FIG. 3. The CPE 200 includes a complementary metal oxide semiconductor (CMOS) optical image sensor 224 mounted thereto. The UV point detectors 222 are used to capture UV-visible point source data. The optical image sensor 224 is used to capture still and/or video images (if power constraints allow) and to transmit this information to a desired device (e.g., a PDA, computer, imager, etc.). The CPE 200 includes a light emitter 205 UV light and visible light by using a UV emitter 230 and a visible light emitter 206), an RF transmitter module 209, an optional receiver (not shown), a power source 210, a power regulator 211, a controller 212, an optional memory (not shown), and filters 226 Moreover, in alternative embodiments, lenses (not shown) may be necessary for each light source and/or each detector, and can include multi-element lenses as well as other suitable lenses which can focus and pass desired wavelengths.

The photo detectors include a CMOS imager 224 and a UV/visible point detector or other suitable photonic detector which is suitable for detecting visible and UV light (fluorescence) being returned from the illuminated biological tissue. Optional wavelength selection components such as gratings and filters are used to filter the light as desired and will not be further described as they have been described elsewhere in this document. Likewise, optional beam steering components can be used to precisely locate and/or focus desired optical beams (and have been described elsewhere in this document and therefore a further description will not be given.

The power source 210 is used to provide power to various components of the CPE 200 and can include storage sources such as a battery, a fuel cell and/or capacitors etc. The optional regulator 211 regulates and controls to the various elements of the CPE 200 as required.

An RF transmitter module 209 is used to transmit data from the CPE 200 to a desired receiver such as a remote or user-worn computer, PDA, etc. The RF transmitter module 209 includes a mixer 213, an oscillator (e.g., a voltage-controlled oscillator (VCO)), and a mixer (e.g., an RF or microwave mixer) for converting base-band signals to RF or microwave signals. The oscillator is preferably a low-power oscillator which can emit one or more desired frequencies suitable for at least RF or microwave transmission.

In alternative embodiments, a plurality of oscillators including a first oscillator and a second oscillator are provided. The first oscillator produces a high frequency signal which is suitable for RF or microwave mixing, and the second oscillator which produces a much lower frequency signal and is used for basic operations (as will be described below). In use, either or both oscillators can be powered on and operated as necessary. For example, when the higher frequency is necessary or desired (e.g., when mixing baseband signals with RF for transmission), the first oscillator is powered on and used by at least the mixer 213. The second oscillator can also be used by any elements of the CPE 200 as desired. By controlling the oscillators, the power draw can be lowered and the duration of the CPE's battery life can be extended. For example, by equipping the CPE with an optional timer, the CPE can enter an optional sleep state in which the first oscillator is switched off and the second oscillator is used by an internal timer (and/or other circuitry) which can conserve power by reducing the clock cycle (and hence reduce the power consumption of clocked transistors). When the CPE awakens from the sleep state (e.g., when the timer determines that it is time to take one or more photographs, transmit data, process/take fluorescence data, etc.), the CPE can activate the first oscillator (and optionally cut the power supply to the second oscillator to conserve power).

The controller 212 includes a micro-processor and is used for controlling the various functions of the CPE 200 including optional timing circuits (not shown) which are used for timing and powering the emitters and for sampling the detectors (e.g., gating the detectors). For example, the controller 212 controls the timing of the visible and UV emitters 206 and 230, respectively, and the gating of the CMOS optical image sensor 224. Moreover, the controller 212 controls the RF transmitter module 209 so that data can be transmitted from the CPE 200 to other locations. The data can be sent in either analog form or in digital form if an analog-to-digital (A/D) converter (not shown) is used.

An optional memory such as a RAM, ROM, etc. (not shown) interfaces with the controller and is used for storing and retrieving necessary data (e.g., code to control the CPE 200, image data, etc. as required).

Figure 4:
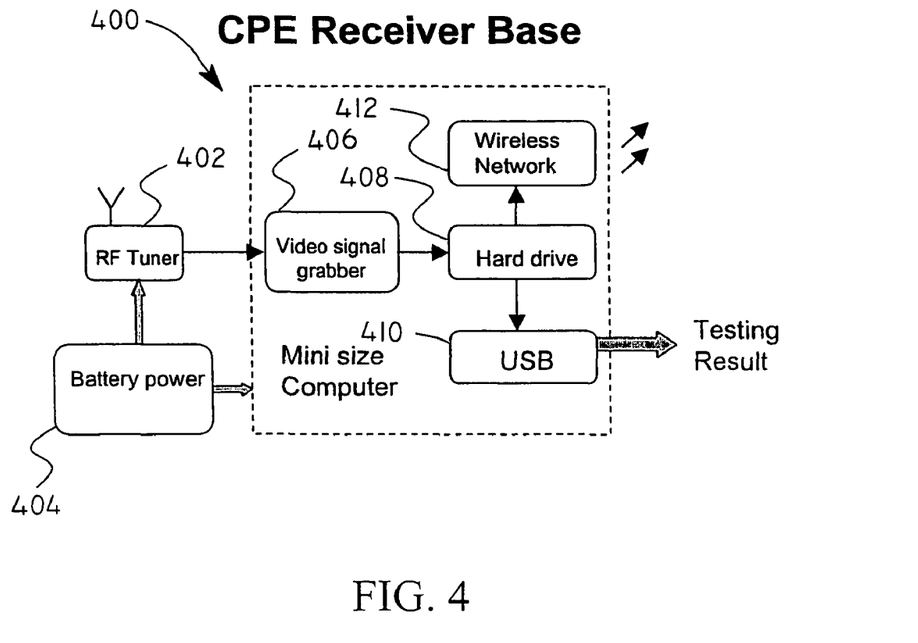
FIG. 4 is a block diagram of a CPE receiver base according to an embodiment the present invention.

A block diagram of a CPE receiver base according to an embodiment of the present invention is shown in FIG. 4. The CPE receiver base 400 includes an RF tuner 402, a power supply 404 (e.g., a battery, capacitor, fuel cell, solar cell, etc.), a video signal grabber 406, a memory (e.g., one or more of a hard drive, RAM, ROM, etc.) 408, an optional wireless network interface 412, and an optional bus (e.g., a universal serial bus (USB)) 410. In operation, the RF tuner 402 receives a transmission (e.g., RF, microwave, etc.) including fluorescence data (and optional image data) from the CPE 200 and converts the received RF signals to baseband signals. The baseband signals are then processed by the video signal grabber 406, which extracts desired data from the baseband signal. The data can then be saved in the memory 408 and/or transmitted to other devices via the USB, Ethernet or fire wire or the wireless network interface 412, as desired.

Figure 5:
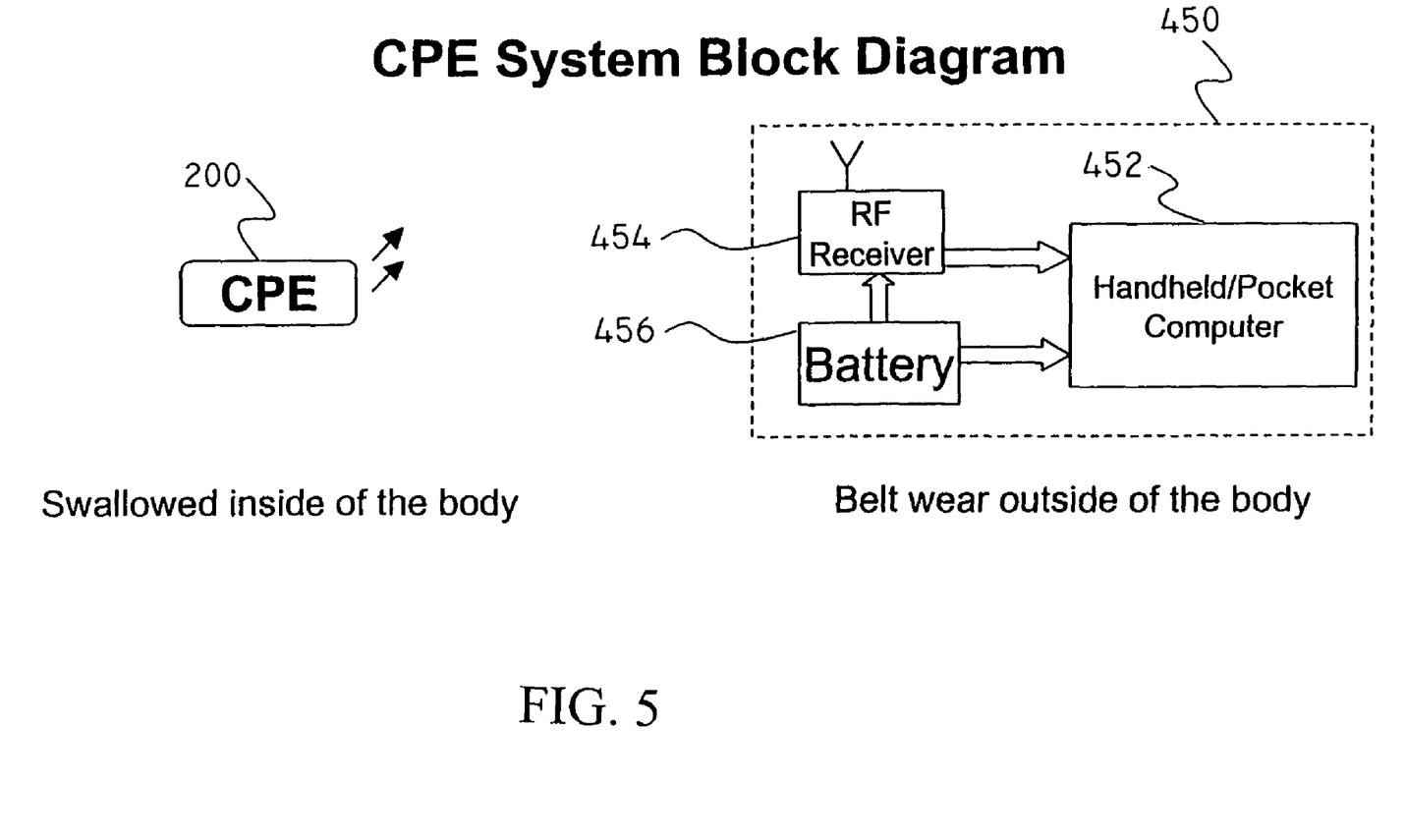
FIG. 5 is a block diagram illustrating a mobile CPE receiver base with a computer system on a belt according to an embodiment of the present invention.

A block diagram illustrating a mobile CPE base according to an embodiment of the present invention is shown in FIG. 5. The mobile CPE base 450 includes a mobile terminal (MT) 452 (e.g., a Palm™-type device such as a PalmOne Tungsten T5 Handheld™, an Apple™ I-Pod™, a Pocket PC LabView, a Dell Axim™ X50v, OQO-μPC mini computer, other palm-type devices using a Palmυ OS or other suitable operating system such as a windows-based operating system, mobile phones, etc.) The MT 452 includes a receiver tuned to CPE 200 for receiving transmissions from the CPE 200, which can located inside a human body during tissue assessment. The MT 452 can also include software for receiving, processing, analyzing, storing, displaying, and transmitting desired data from the CPE 200. For example, software for processing digital data received from the CPE 200 can include digital signal processing (DSP) technologies which can improve the clarity of the images received from the CPE 200. Moreover, the software can include algorithms to enable the MT 452 to calculate the FIR.

The MT 452 can include extra receivers (which can be releasably attached to the user of the CPE 200) which would enable the MT 452 to locate the CPE 200 within the user's body. This location data can then be associated with any of the image, fluorescence, or FIR data. Depending upon the application an optional power supply may be required to power the receiver and/or the MT.

In alternative embodiments, it is envisioned that the MT 452 can use an existing wireless network to transfer images and data that are received from the CPE 200 to a server or other computer device for processing and analysis. For example, the MT can transfer images directly to a medical provider's office computer for real-time analysis by a doctor. This can obviate or shorten a user's visit to a medical provider's office.

In yet other alternative embodiments, the MT 452 can also acquire, process and/or transmit other user data. For example, the MT 452 can acquire a user's heartbeat, temperature, blood oxygen level, etc. as desired A possible combination of emitters and detectors can be based on fluorescence spectra acquired and analyzed in prior studies on aerodigestive tract tissues performed in vivo (i.e., "In Vivo Native Cellular Fluorescence And Histological Characteristics Of Head And Neck Cancer," Clinical Cancer Research. 4: 1177, 1998, by Schantz, S. P., Kolli, V., Savage, H. E., Yu, G., Shah, J. P., Harris, D., Katz, A. Alfano, R. R. and G., H. A.) and ex vivo (i.e., Investigation Of Barrett's Esophagus By Ultraviolet And Visible Fluorescence Emission And Excitation Spectroscopy," Optical Tomography and Spectroscopy of Tissue III, SPIE Proceedings Vol. 3597, San Jose, 1999 by Katz, A., Savage, H. E., Chu, M., Busuk, P. M., Altorki, N., Godwin, T., McCormick, S. A., and Alfano, R. R.; and "Excitation Spectrum Of Malignant And Benign Breast Tissues: A Potential Optical Biopsy Approach," Lasers In The Life Sciences, 7,(4):249-65, 1997 by Y. Yang, Y., E. J. Celmer, M. Zurawska-Szczepaniak, and R. R. Alfano), the contents of both of which are incorporated herein by reference.

Figure 6:
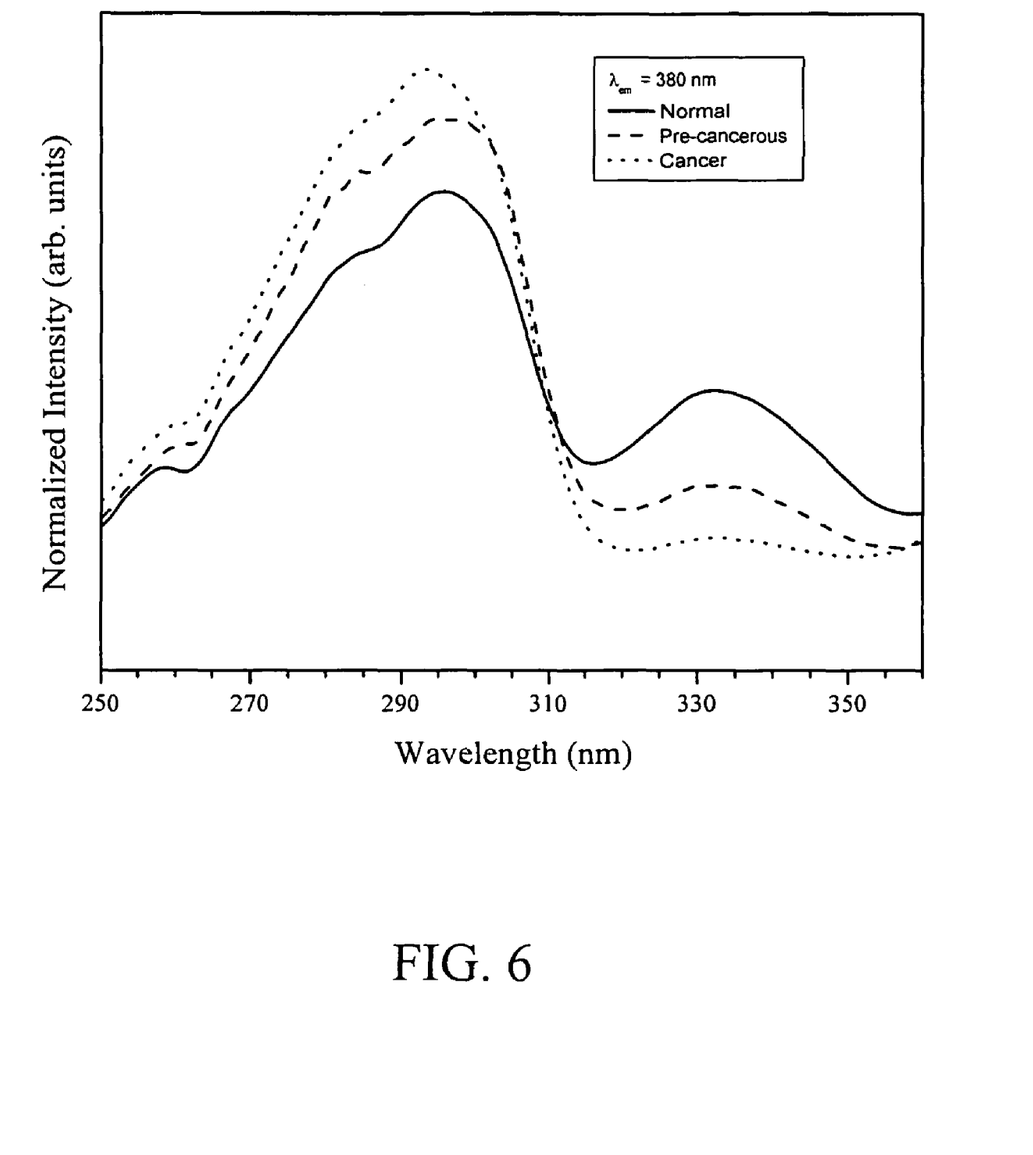
FIG. 6 is a graph illustrating the averaged emission spectra from normal, pre-cancerous (dysplasia) and cancerous (adenocarcinoma) ex vivo esophageal tissues.

A graph illustrating the averaged emission spectra from normal, pre-cancerous (dysplasia) and cancerous (adenocarcinoma) ex vivo esophageal tissues attained using an alternative embodiment of the present invention is shown in FIG. 6. The current embodiment includes only one excitation source at 320 nm and two detectors with filters for different wavelengths of 380 nm and 460 nm, respectively. The present emitter/detector combination is ideal for measuring the emission and to calculate the intensity ratios from collagen and NADH. The graph shows the normalized emission spectra from normal, precancerous and cancerous ex vivo esophageal tissues, and shows the relative differences in intensity of these bands.

Figure 7:
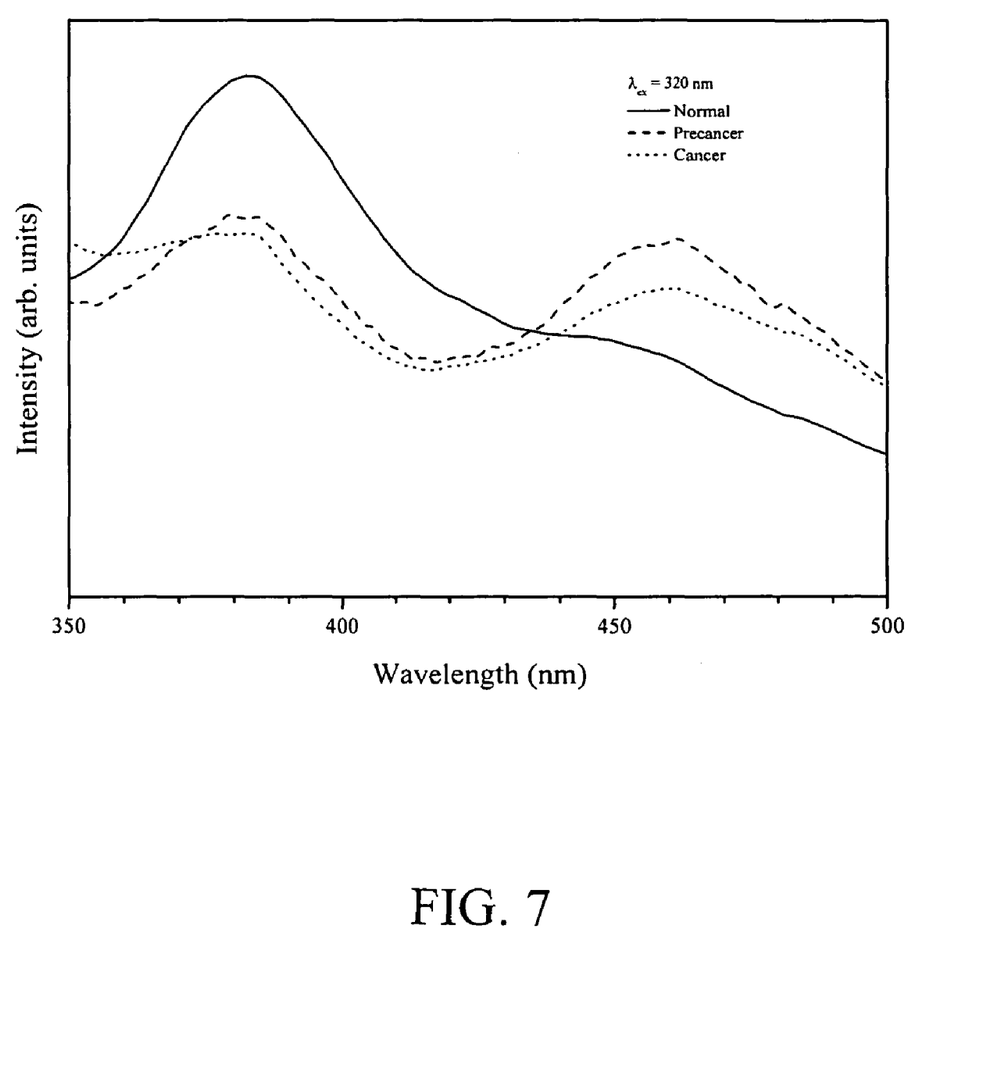
FIG. 7 is a graph illustrating the averaged excitation spectra from normal, pre-cancerous (dysplasia) and cancerous (adenocarcinoma) ex vivo esophageal tissues.

A graph illustrating the averaged excitation spectra from normal, pre-cancerous (dysplasia) and cancerous (adenocarcinoma) ex vivo esophageal tissues attained using an embodiment of the present invention, is shown in FIG. 7. A method for selecting the emitter and detector wavelengths determined from analysis of the fluorescence spectra can be seen by examining the normalized, average excitation spectra from normal, cancerous, and precancerous esophageal tissue. To obtain these measurements, the excitation spectra were scanned from 250-360 nm while the emission intensity at 380 nm was measured. The band excited at 290 nm is from tryptophan and the band excited at 335 nm, and only present in normal tissue, is from collagen. A ratio of tryptophan to collagen emission intensity can be calculated by the ratio of the 380 nm emission with the 290 nm excitation to the 380 nm emission with the 335 nm excitation. For cancerous and precancerous tissue, this ratio will be high due to the weak collagen emission. For normal tissue, this ratio will be low due to the presence of a strong collagen emission. This ratio can be determined in the CPE by the use of two emitters at 390 and 335 nm and one detector at 380 nm. The tryptophan and collagen signals can be separated by pulsing the excitation sources at different times, and gating the detector.

Two methods used to obtain a fluorescence intensity ratio (FIR) are known as the emission ratio method and the excitation ratio method. Either one gives diagnostic information about malignancy. The emission ratio method uses a single excitation wavelength, (e.g., from a single UV LED), detects the fluorescence emission intensity at two different wavelengths (using at least two UV-visible detectors) and computes a ratio of the detected emission intensity using the detected fluorescence emission intensities. The excitation ratio uses at least two excitation wavelengths (e.g., from two UV LEDs having different wavelengths) and detects (e.g., using a single detector) the fluorescence emission intensity for each of the excitation wavelengths. The fluorescence emission intensity ratio is then computed using the two fluorescence emission intensities.

In alternative embodiments, a UV dye can be used to cause tissue to fluoresce at a frequency other than a native frequency.

Figure 8:
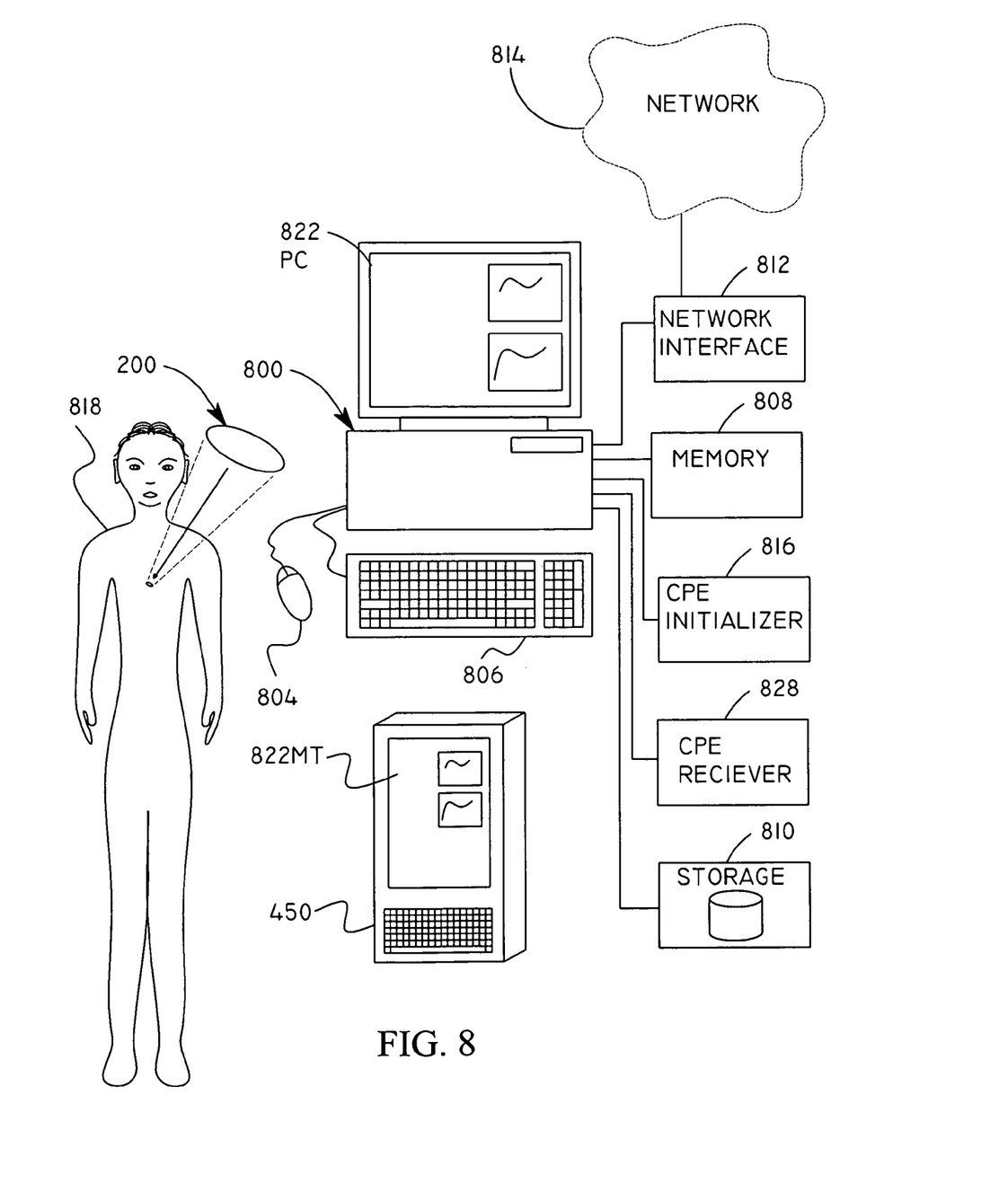
FIG. 8 is a block diagram of a reception/control apparatus with a desktop computer according to an embodiment of the present invention.

A block diagram of a system including the CPE according to an embodiment of the present invention is shown in FIG. 8. The system includes a computer such as a PC 800 using an operating system (e.g., Windows™, Unix, Linux, etc. as desired). The PC includes one or more input devices such as a keyboard 806 and a mouse 804, a memory 808, an optional disk storage means such as a hard-drive 810, an optional network interface 812 for connection to external devices including networks 814, and an optional CPE receiver 828 and optional transmitter 816 for transmitting communications from/to the CPE 200. Additionally, a mobile CPE receiver base 450 may be used. In use, the CPE 200 is inserted into a patient 818 (which is not limited to humans), and an operator of the PC controls and/or receives information from the CPE 200. For example, still images, graphs and other data can be displayed on a display 822PC and/or the mobile CPE receiver base screen 822MT. Although the PC 800 is shown next to the patient 818, in alternative embodiments, the operator can be located anywhere in the world as is technologically feasible using network communication. In yet alternative embodiments, data can be transmitted from the CPE 200 to the PC 800 which then transmits selected data to a computer located anywhere in the world. For example, a patient located in Antarctica can swallow a CPE 200. The CPE is locally controlled by a nearby computer being in RF communication with the CPE. The first computer communicates with one or more operators, one of whom may be located in New York, U.S.A. and translates still images received from image data received from the CPE. Another operator may be located in New Deli, India and translates fluorescence data received from the CPE. Image data and other data from the CPE can also be stored in a database for later use. In some uses, the CPE 200 transmits data to the mobile CPE receiver base 450 which then optionally transmits the data to the PC. The CPE 200 can also transmit data directly to the PC via the CPE receiver 828.

Figure 9:
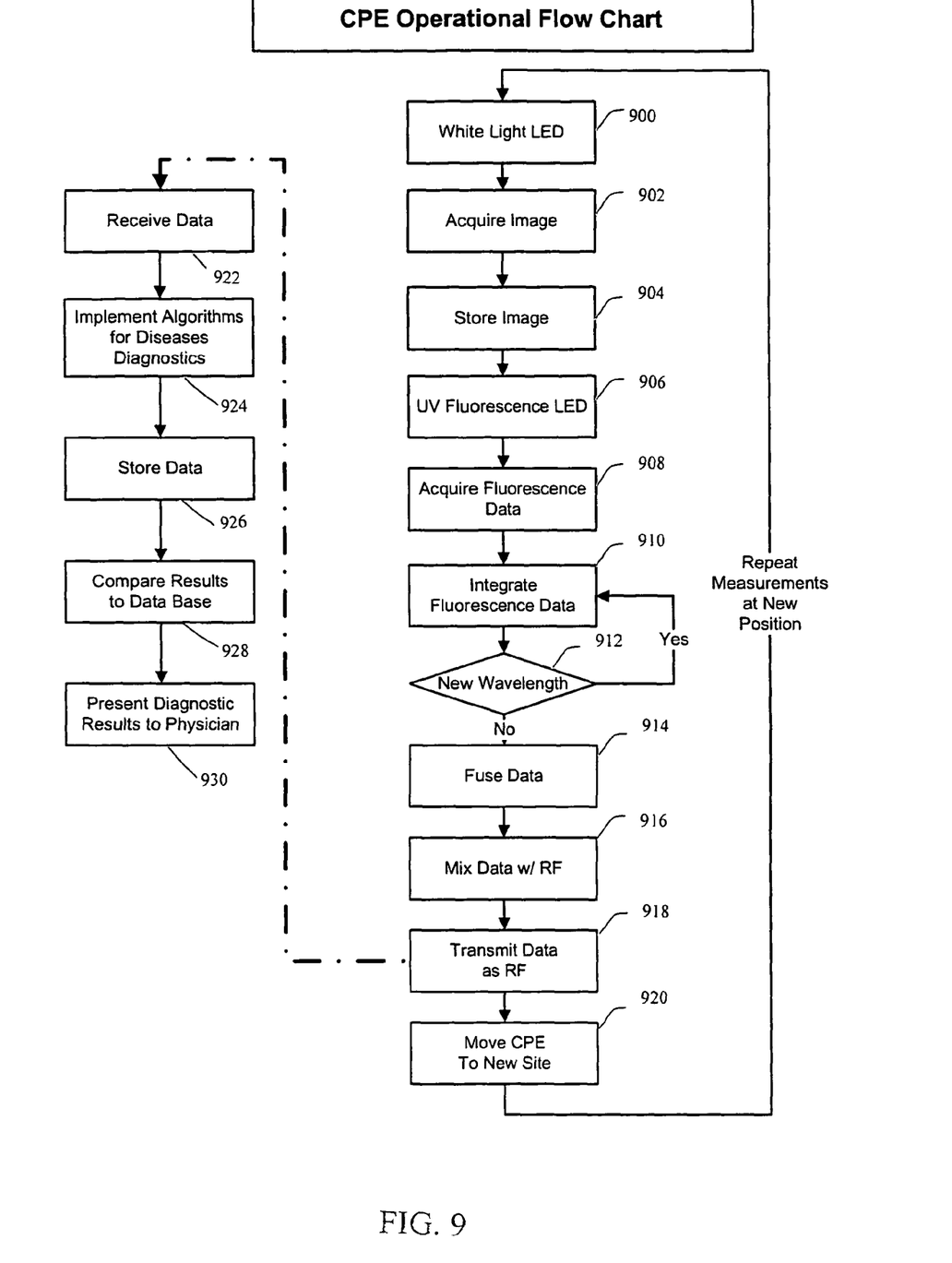
FIG. 9 is a flowchart illustrating the operation of the CPE according to an embodiment of present invention.

A flowchart illustrating the operation of an embodiment of the CPE is shown in FIG. 9. After the CPE is initialized, it is inserted into a body. In step 900, (assuming the controller 212 has already determined that it is the proper time to start an image capture routine) the controller 212 causes the visible light emitter 206 (which in this example is a white light LED) to illuminate biological tissue. The controller 212 then proceeds to step 902, where a visible image is captured by the optical image sensor 224. The image is then stored in a memory 218 in step 904. UV emitters are then activated to emit UV light to cause the biological tissue to fluoresce in step 906. The UV emitters can be activated either sequentially or all together depending upon wavelength and noise characteristics. In step 908, fluorescence data is captured by at least one of the UV detectors 222-1, 222-2 and 222-3. In alternative embodiments the optical image sensor 224 captures the fluorescence data. In step 910, the captured fluorescence data is integrated i.e., multiple UV image data is integrated until a given threshold is met in step 912. For example, a given threshold can include a predetermined number of data samples N, a signal threshold, a signal/noise ratio, a given number of captured UV wavelengths, a desired fluorescence intensity ratio, etc. as desired. After the fluorescence data is integrated and no new fluorescence data is required, the fluorescence data is optionally fused to the image data in step 914. The fluorescence data can be fused to an image by adding the data to the actual image data, by serially adding the fluorescence data to the image data, or by any other suitable method wherein the fluorescence data can be associated with its corresponding visual image. In alternative embodiments, the fluorescence data is fused by an external computer such as the mobile CPE receiver base 450 or PC 800.

In step 916, either or both of the visual image data and the respective fluorescence data are mixed with an RF signal or any other suitable signal for transmission in step 918. In step 920 the CPE 200 is moved to another site and the image/fluorescence data capture process is repeated. Suitable methods for moving the CPE 200 can include passive and active motive means (e.g., gas pressure, magnetic force, etc.), As described above. An optional timer can be activated after the aforementioned image/fluorescence data capture process is performed, so that the CPE has time to move to a new location before the image/fluorescence data process is repeated in step 900.

The process of data reception is illustrated in steps 922 to 930. For illustration only, it will be assumed that the receiver is a mobile CPE receiver base 450 as described above. In step 922, data transmitted from the CPE 200 is received. The received data is then processed in step 924 using, for example, algorithms for disease diagnostics, digital signal processing (DSP) routines, etc. In step 926, the received data is optionally stored in a memory. In step 928, the received data is compared with other data which is stored in a database. In step 930, the results of the operations which were performed upon the received data are optionally displayed for use by a physician.

During the image-capture process, external systems can provide data on the location of the CPE. This data can further be linked to the actual visual image data and to the fluorescence data so that a medical provider can associate an image and other data with a location.

The location of the CPE can be determined by, among other methods, detecting a phase-shift in the CPE's transmission signal. This would require several receivers, which could be mounted on or about a patient. For example, the mobile CPE receiver base 450 can be coupled to several receivers (not shown) which are releasably attached to the user at various locations on the user's body. The receivers would then receive the signal from the CPE 200 and forward this signal to the mobile CPE receiver base 450 via an RF link, an optical link, a hardwired link, etc. as desired, for analysis. The location data can then be linked to the received data.

It should be noted that the emitters can be sequentially cycled so that the UV emissions (i.e., the emitted light) do not interfere with each other.

Figure 10:
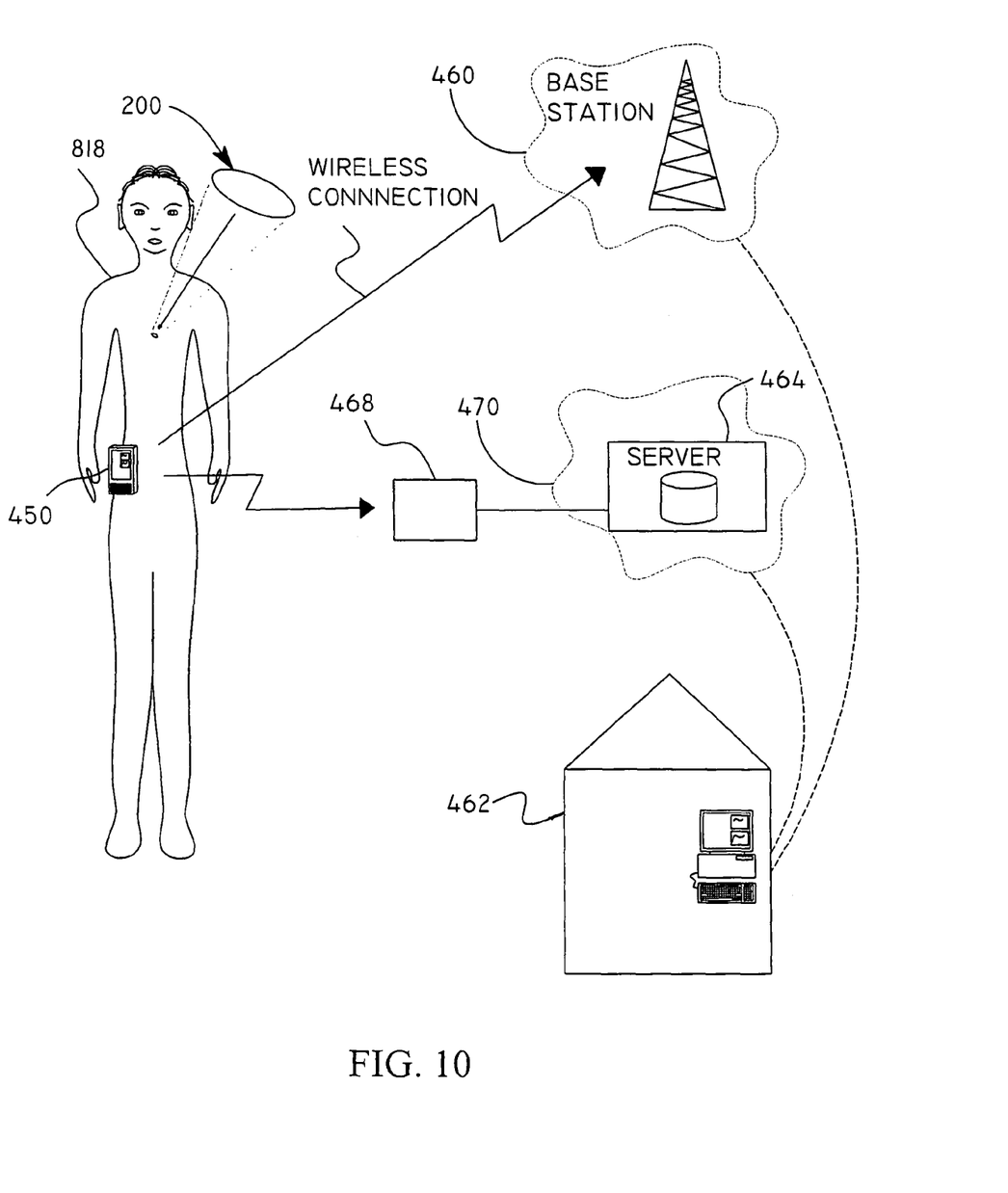
FIG. 10 is an illustration of the CPE and the mobile CPE base receiver in use according to an embodiment of the present invention.

An illustration of the CPE 200 and the mobile CPE receiver base 450 including an MT 452 in use according to an embodiment of the present invention is shown in FIG. 10. In use the CPE 200 is programmed and inserted into a desired location or swallowed by a user 818. The user 818 wears the MT 452 in a desired location using a belt or other suitable device for locating the MT 452 in a desired location relative to the user. The CPE 200 transmits data from within the user, and the MT 452 receives the data. The MT 452 can then retransmit the data, store the data, process the data and/or display the data as desired. For example, the MT 452 can send some data using a cellular communication system 460 to a medical provider 462, and other data can be sent to a server 464 via a wireless networking system 468 and the Internet 470, for later use by the medical provider.

While the above description contains many specifics, these specifics should not be construed as limitations of the invention, but merely as exemplifications of preferred embodiments thereof. Those skilled in the art will envision may other embodiments within the scope and spirit of the invention.

What is claimed is:

1. An apparatus for visually assessing and detecting abnormalities in biological tissue in vivo, the apparatus comprising:
    an emitter for emitting a plurality of ultra-violet (UV) light beams having different excitation wavelengths suitable for causing biological tissue to emit fluorescence at an emission wavelength, wherein the emitter comprises a plurality of light-emitting diodes (LEDs) and each of the plurality of LEDs emits a UV light beam at a different wavelength of a plurality of predetermined wavelengths so as to be able to excite different tissue fluorophores;
    a detector for detecting the fluorescence;
    a controller for controlling the emitter and detector;
    a transmitter for transmitting data received from the detector to a remote receiver, the transmitter being controlled by the controller; and
    a transport capsule for containing at least the emitter, the detector, the controller and the transmitter.

2. The apparatus according to claim 1, wherein each of the LEDs is activated at any given time exclusive of at least one of the other LEDs so as to reduce crosstalk between optical wavelengths.

3. The apparatus according to claim 1, further comprising a visible light (VL) emitter and an optical image sensor for visible light imaging, the VL emitter including a white-light LED.

4. The apparatus according to claim 1, wherein the detector includes a plurality of photodetectors, with each of the plurality of photodetectors being capable of detecting at least a different predetermined wavelengths, so that the detector is capable of detecting a plurality of emission wavelengths.

5. The apparatus according to claim 1, wherein the emitter includes at least one LED and the detector includes at least one photodetector, the number of LEDs and the number of photodetectors are selected so as to match the number of fluorescent wavelengths having desired diagnostic information.

6. The apparatus according to claim 1, further comprising at least one optical filter for filtering the emission wavelengths and allowing only one or more desired emission wavelengths to be detected by the detector.

7. The apparatus of claim 1, wherein the plurality of LEDs are based on alloys of AlGaN.

8. The apparatus of claim 1, wherein the plurality of predetermined wavelengths are between 265 and 325 nm.

9. The apparatus according to claim 1, further comprising a visible light (VL) emitter and an optical image sensor for visible light imaging, the VL emitter including a plurality of LEDs.

10. The apparatus according to claim 9, wherein VL emitter includes a red LED, a blue LED and a green LED.

11. The apparatus according to claim 1, wherein the emitter includes at least one LED and the detector includes at least one photodetector, the number of LEDs and the number of photodetectors are selected so as to at least be able to excite multiple tissue fluorophores and detect the corresponding fluorescence.

12. The apparatus according to claim 11, wherein the tissue fluorophores include at least one of tryptophon, tyrosine, collagen, elastin and NADH.

13. A method for visually assessing and detecting abnormalities in biological tissue in vivo using a capsule, the method comprising the steps of:
emitting a plurality of ultra-violet (UV) light beams from the capsule having excitation wavelengths suitable for causing biological tissue to emit native fluorescence at an emission wavelength, wherein the light beams are directed at the biological tissue, each of the plurality of light beams has a different wavelength of a plurality of predetermined wavelengths so as to be able to excite different tissue fluorophores, and each of the plurality of light beams is emitted from a different one of a plurality of light-emitting diodes (LEDs);
detecting the fluorescence from biological tissue using at least one detector; and
transmitting data related to the detected fluorescence to a remote receiver.

14. The method according to claim 13, wherein visible light (VL) is created using a single white-light LED and a visible image is captured using an optical image sensor.

15. The method according to claim 13, wherein a visual image of the biological tissue is obtained and the presence of at least one of cancer and precancer of the biological tissue can be determined, by:
illuminating the biological tissue with visible light and obtaining a visible light image of the biological tissue;
exciting the biological tissue using at least two excitation wavelengths so that the biological tissue emits fluorescence at a given emission wavelength corresponding to the at least two excitation wavelengths;
detecting the intensity of the fluorescence at an emission wavelength for each of the excitation wavelengths; and
comparing a ratio of the detected intensities to a predetermined threshold to determine the presence of at least one of cancer or precancer.

16. The method of claim 13, wherein the plurality of LEDs are based on alloys of AlGaN.

17. The method of claim 13, wherein the plurality of predetermined wavelengths are between 265 and 325 nm.

18. The method according to claim 13, further comprising emitting visible light (VL) light created using a plurality of LEDs and capturing a visible image using an optical image sensor.

19. The method according to claim 18, wherein the emission wavelength includes a plurality of wavelengths, and a number of emitters and a number of detectors are selected so as to match a number of wavelengths having desired diagnostic information.

20. A method for receiving image and fluorescence data taken from biological tissue in vivo, the method comprising the steps of:
emitting a plurality of ultra-violet (UV) light beams from a capsule, the light beams having excitation wavelengths suitable for causing biological tissue to emit fluorescence at an emission wavelength, wherein each of the plurality of light beams has a different wavelength of a plurality of predetermined wavelengths so as to be able to excite different tissue fluorophores, and each of the plurality of light beams is emitted from a different one of a plurality of light-emitting diodes (LEDs);
receiving data related to detected fluorescence from the capsule; and
processing the received data to determine a fluorescence intensity ratio (FIR).

21. A Mobile terminal (MT) apparatus for receiving image data including fluorescence data for visually assessing and detecting abnormalities in biological tissue in vivo, the apparatus comprising:
a capsule configured to emit ultra-violet (UV) light beams having excitation wavelengths suitable for causing biological tissue to emit fluorescence at an emission wavelength, wherein each of the plurality of light beams has a different wavelength of a plurality of predetermined wavelengths so as to be able to excite different tissue fluorophores, and each of the plurality of light beams is emitted from a different one of a plurality of light-emitting diodes (LEDs);
a receiver for receiving image and fluorescence data transmitted from the capsule device;
a processor for processing the image and fluorescence data received from the capsule device; and
a transmitter for transmitting the received image and fluorescence data.

* * * * *